US012201701B2

(12) United States Patent
Lee et al.

(10) Patent No.: US 12,201,701 B2
(45) Date of Patent: Jan. 21, 2025

(54) VEGETABLE OIL-DERIVED CONTRAST AGENT WITH HIGH STABILITY AND PREPARATION METHOD THEREOF

(71) Applicant: ENGAIN CO., LTD., Seongnam-si (KR)

(72) Inventors: Won Mok Lee, Seoul (KR); Kyoung Ho Kim, Seoul (KR); Young Gook Koh, Seongnam-si (KR); Ha Been Park, Yongin-si (KR)

(73) Assignee: ENGAIN CO., LTD., Seongnam-si (KR)

( * ) Notice: Subject to any disclaimer, the term of this patent is extended or adjusted under 35 U.S.C. 154(b) by 0 days.

(21) Appl. No.: 17/319,912

(22) Filed: May 13, 2021

(65) Prior Publication Data

US 2022/0339299 A1    Oct. 27, 2022

(30) Foreign Application Priority Data

Apr. 22, 2021    (KR) .................. 10-2021-0052133

(51) Int. Cl.
*A61K 49/04*    (2006.01)
(52) U.S. Cl.
CPC .................. *A61K 49/0438* (2013.01)
(58) Field of Classification Search
CPC ................................................ A61K 49/0438
See application file for complete search history.

(56) References Cited

U.S. PATENT DOCUMENTS

2003/0228273 A1* 12/2003 Greff ................ A61K 31/78
424/78.35

FOREIGN PATENT DOCUMENTS

| CN | 101676255 A | 3/2010 |
|---|---|---|
| CN | 101245002 B | 3/2011 |
| CN | 105062693 B | 11/2015 |
| CN | 107287029 A | 10/2017 |
| EP | 0198344 A1 * | 10/1986 |
| EP | 3428256 A1 | 1/2019 |
| JP | S62285995 A | 12/1987 |
| JP | 2014068541 A | 4/2014 |
| KR | 1020150068238 A | 6/2015 |
| KR | 1020180035971 A | 4/2018 |
| KR | 102102533 B1 | 4/2020 |

OTHER PUBLICATIONS

Guerbet, Jul. 1, 2013, https://www.fda.gov/media/79119/download. (Year: 2013).*
Dubbelboer et al., Therapeutic Delivery, 2014, 5(4), p. 447-466. (Year: 2014).*
IARC Working Group on the Evaluation of Carcinogenic Risks to Humans, Occupational Exposures to Mists and Vapours from Strong Inorganic Acids; and Other Industrial Chemicals. Lyon (FR): International Agency for Research on Cancer; 1992. (Year: 1992).*
Med Lab Supply, 2018, https://www.blog.medical-and-lab-supplies.com/questions-you-may-have-about-ethyl-oleate/. (Year: 2018).*
Kuhn et al., EP0198344A1, 1986 (English translation). (Year: 1986).*
Lin et al., CN 112300868, Feb. 2, 2021 (English translation). (Year: 2021).*
Bronste-Lowry Acid-Base Theory, https://en.wikipedia.org/w/index.php?title=Br%C3%B8nsted%E2%80%93Lowry_acid%E2%80%93base_theory&oldid=872086234, Dec. 5, 2018. (Year: 2018).*
Howard F. Martin et al., "Bronchographic Contrast Mediums", Calif Med., 1962, vol. 97(5), pp. 293-297.
Giese J. et al., "Antioxidants: Tools for Preventing Lipid Oxidation Antioxidants are critical in preserving lipid-ocntaining foods from rancidity and extending shelf life", Food Technology, Institute of Food Technologists, Chicago, IL, US, vol. 5, No. 11, Nov. 1, 1996.
Sandeep Nema et al., "Excipients: Parenteral Dosage Forms and Their Role", Encyclopedia of Pharmaceutical Technology Third Ed., Jan. 1, 2006, vol. 43, pp. 1622-1645.
Lemonia Birikaki, "European Search Report for EP Application No. 21174808.2", Oct. 27, 2021, EPO, Munich, Germany.

* cited by examiner

*Primary Examiner* — Michael G. Hartley
*Assistant Examiner* — Leah H Schlientz
(74) *Attorney, Agent, or Firm* — Bridgeway IP Law Group, PLLC; Jihun Kim

(57) ABSTRACT

Proposed are a contrast agent containing an iodinated unsaturated fatty acid ethyl ester derived from vegetable oil, a non-iodinated unsaturated fatty acid ethyl ester, and sulfur dioxide ($SO_2$), and a production method thereof. The contrast agent having a similar contrast effect is synthesized using vegetable oil as a substitute for poppy seed oil, which is unstable in terms of supply and is expensive. In addition, the long-term stability problem of an iodine-based contrast agent is solved by adding a non-iodinated unsaturated fatty acid ethyl ester and sulfur dioxide.

4 Claims, 19 Drawing Sheets

VEGETABLE OIL-DERIVED CONTRAST AGENT WITH HIGH STABILITY AND PREPARATION METHOD THEREOF

CROSS-REFERENCE TO RELATED APPLICATION

This application claims priority from and the benefit of Korean Patent Application No. 10-2021-0052133, filed on Apr. 22, 2021, which is hereby incorporated by reference for all purposes as if set forth herein.

BACKGROUND

Field

The present disclosure relates to a vegetable oil-derived contrast agent with improved stability, and more particularly, to a contrast agent with improved stability in which a non-iodinated unsaturated fatty acid ethyl ester and sulfur dioxide ($SO_2$) are added to an iodinated unsaturated fatty acid ethyl ester derived from vegetable oil, and a method for producing the same.

Discussion of the Background

Lipiodol, a liver cancer contrast agent produced and sold by the global pharmaceutical Guerbet, is an iodized fatty acid ethyl ester of poppy seed oil, which is used for imaging tests and transcatheter arterial chemoembolization (TACE).

In recent years, as the cancer incidence has increased, the demand for contrast agents such as Lipiodol has increased. However, Lipiodol has a disadvantage in that it is not unstable in terms of supply and is expensive, because poppy seed oil which is used as the raw material thereof is rare and expensive. For this reason, in the related field, efforts have been made to develop an iodized fatty acid ethyl ester that may be used as a substitute for Lipiodol and at the same time, synthesized from an economical and easily available vegetable oil.

One of the general problems of the iodized fatty acid ethyl ester is a stability problem of iodine bound to a contrast agent. That is, when the storage period of the contrast agent is prolonged, a problem arises in that iodine is released from the fatty acid ethyl ester, causing discoloration of the contrast agent, resulting in a rapid decrease in the quality of the contrast agent.

SUMMARY

An object of the present disclosure is to provide a highly stable contrast agent which has X-ray impermeability similar to that of Lipiodol and, at the same time, may be obtained using an easily available and inexpensive vegetable oil instead of poppy seed oil, which is unstable in terms of supply and is expensive, and a method for preparing the same.

Objects of the present disclosure are not limited to the above-mentioned object, and other problems not mentioned herein will be clearly understood to those skilled in the art from the following description.

To achieve the above object, in accordance with one aspect of the present disclosure, there is provided a contrast agent containing: an iodinated unsaturated fatty acid ethyl ester derived from vegetable oil; a non-iodinated unsaturated fatty acid ethyl ester; and sulfur dioxide ($SO_2$).

In one embodiment, the vegetable oil may be at least one vegetable oil selected from the group consisting of sunflower seed oil, soybean oil, peanut oil, walnut oil, sesame oil, castor oil, cottonseed oil, rapeseed oil, flaxseed oil, corn oil, canola oil, palm oil, olive oil, coconut oil, rice bran oil, and grape seed oil.

In one embodiment, the unsaturated fatty acid ethyl ester derived from vegetable oil may contain ethyl oleate.

In one embodiment, the non-iodinated unsaturated fatty acid ethyl ester may be contained in an amount of more than 0 wt % and not more than 10 wt % based on the total weight of the contrast agent.

In one embodiment, the sulfur dioxide may be contained in an amount of more than 0 wt % and not more than 0.1 wt % based on the total weight of the contrast agent.

In accordance with another aspect of the present disclosure, there is provided a method for preparing a contrast agent, the method including steps of: preparing an unsaturated fatty acid ethyl ester from vegetable oil by a transesterification reaction; preparing an iodinated unsaturated fatty acid ethyl ester by subjecting the unsaturated fatty acid ethyl ester to an iodination reaction; and adding a non-iodinated unsaturated fatty acid ethyl ester and sulfur dioxide ($SO_2$) to the iodinated unsaturated fatty acid ethyl ester.

In one embodiment, the transesterification reaction may be performed by adding ethanol and a strong base to the vegetable oil.

In one embodiment, glycerol and saturated fatty acid ethyl ester may be removed after the transesterification reaction.

In one embodiment, the iodination reaction may be performed by adding gaseous hydrogen iodide (HI) to the unsaturated fatty acid ethyl ester.

In one embodiment, the iodination reaction may be followed by first purification with a base and second purification silica gel.

DETAILED DESCRIPTION OF THE ILLUSTRATED EMBODIMENTS

Figure 1:
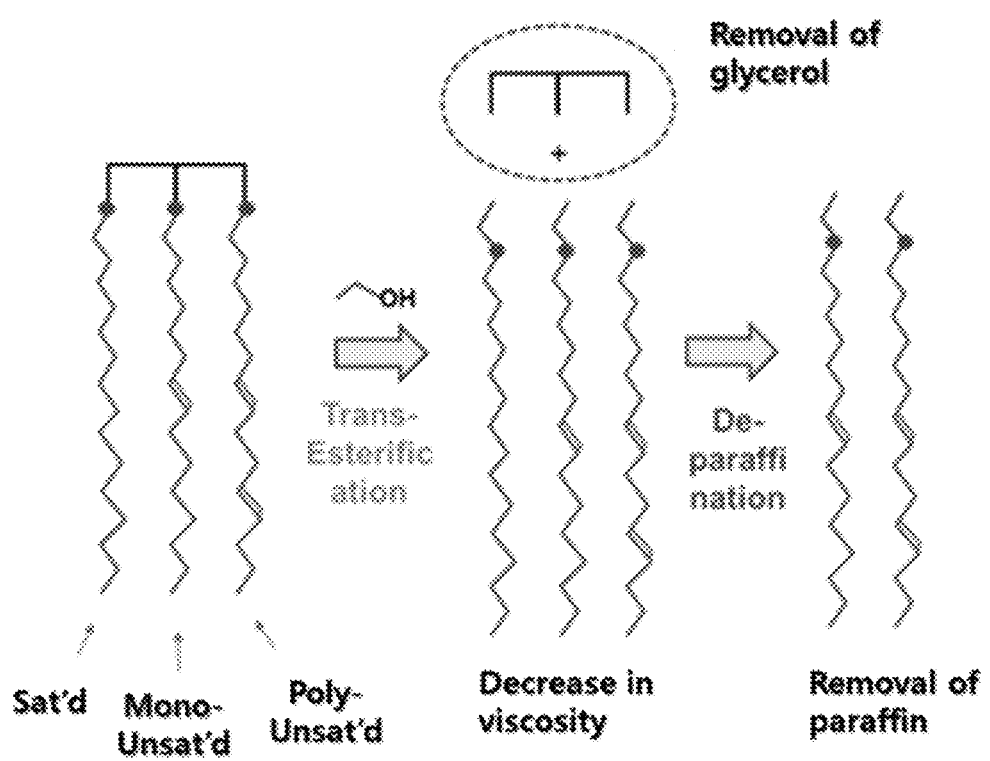
FIG. 1 is a conceptual view showing a method of performing a transesterification reaction on vegetable oil.

The present disclosure provides contrast agent containing: an iodinated unsaturated fatty acid ethyl ester derived from vegetable oil; a non-iodinated unsaturated fatty acid ethyl ester; and sulfur dioxide ($SO_2$).

The iodinated unsaturated fatty acid ethyl ester derived from vegetable oil, which is contained in the contrast agent of the present disclosure, may be prepared by subjecting the vegetable oil to transesterification and iodination reactions. A method for preparing the iodinated unsaturated fatty acid ethyl ester will be described in detail below.

The vegetable oil that is used in the present disclosure may be used without limitation as long as it is a vegetable oil containing an unsaturated fatty acid capable of reacting with iodine. For example, the vegetable oil may be at least one vegetable oil selected from the group consisting of sunflower seed oil, soybean oil, peanut oil, walnut oil, sesame oil, castor oil, cottonseed oil, rapeseed oil, flaxseed oil, corn oil, canola oil, palm oil, olive oil, coconut oil, rice bran oil, and grape seed oil, but is not limited thereto. Preferably, sunflower seed oil or soybean oil having a saturated fat-to-unsaturated fat ratio similar to that of poppy seed oil may be used.

The non-iodinated unsaturated fatty acid ethyl ester contained in the contrast agent of the present disclosure is added to increase the long-term stability of the contrast agent. The non-iodinated unsaturated fatty acid ethyl ester reacts with iodine decomposed in the iodinated unsaturated fatty acid ethyl ester, thus preventing browning caused by iodine. Thus, the non-iodinated unsaturated fatty acid ethyl ester may be used without limitation as long as it is any fatty acid ethyl ester having an unsaturated bond. Preferably, a fatty acid ethyl ester may be used which has the same chemical structure as the iodinated unsaturated fatty acid ethyl ester except for the iodinated portion.

In the present disclosure, the non-iodinated unsaturated fatty acid ethyl ester may be used in an amount capable of reacting with free iodine without changing the contrast effect of the contrast agent. Preferably, the non-iodinated unsaturated fatty acid ethyl ester may be used in an amount of more than 0 wt % and not more than 10 wt %, more preferably 0.1 to 2 wt %, based on the total weight of the contrast agent.

Sulfur dioxide contained in the contrast agent of the present disclosure is added to increase the long-term stability of the contrast agent. The sulfur dioxide serves as an antioxidant and an anion inhibitor and to prevent browning caused by iodine by suppressing the decomposition of iodine in the iodinated unsaturated fatty acid ethyl ester. To this end, the sulfur oxide in the present disclosure may be contained in an amount of more than 0 wt % and not more than 0.1 wt %, preferably 0.001 to 0.02 wt %, based on the total weight of the contrast agent.

The present disclosure also provides a method for preparing a contrast agent, the method including steps of: preparing an unsaturated fatty acid ethyl ester from vegetable oil by a transesterification reaction; preparing an iodinated unsaturated fatty acid ethyl ester by subjecting the unsaturated fatty acid ethyl ester to an iodination reaction; and adding a non-iodinated unsaturated fatty acid ethyl ester and sulfur dioxide ($SO_2$) to the iodinated unsaturated fatty acid ethyl ester.

The method for preparing the contrast agent according to the present disclosure includes a step of preparing an unsaturated fatty acid ethyl ester from vegetable oil by a transesterification reaction. The transesterification reaction in this step is schematically illustrated in FIG. 1. The components of the vegetable oil are triglycerides composed of three molecules of fatty acids joined to one molecule of glycerol through ester bonds. The transesterification reaction of vegetable oil is performed by addition of an alcohol in the presence of a strongly basic catalyst. Triglycerides are hydrolyzed into glycerol and fatty acids by the strong base, and the hydrolyzed fatty acids are ester-bonded to the alcohol, thus synthesizing a fatty acid ester.

In the present disclosure, the alcohol that is used in the transesterification reaction may be methanol or ethanol. Preferably, the alcohol may be ethanol suitable for medical use. When ethanol is used, a fatty acid ethyl ester is prepared.

In the present disclosure, the basic catalyst that is used in the transesterification reaction may be the strong base sodium hydroxide, potassium hydroxide, barium hydroxide or calcium hydroxide, but is not limited thereto. Preferably, potassium hydroxide having relatively low deliquescence may be used to suppress a saponification reaction.

The method for preparing the contrast agent according to the present disclosure includes a purification process of removing glycerol and a saturated fatty acid ethyl ester after the transesterification reaction. After the transesterification reaction, the remaining alcohol, strong base and by-product glycerol are preferentially removed. In addition, since the vegetable oil contains saturated fatty acids that cannot be combined with iodine, a purified unsaturated fatty acid ethyl ester may be obtained by removing the fatty acid ethyl ester prepared from the saturated fatty acid among the fatty acid ethyl esters. The transesterification reaction and the purification process will be described in detail in the following examples.

Through the above-described process, it is possible to prepare an unsaturated fatty acid ethyl ester based on an ethyl oleate made of a monounsaturated fatty acid of vegetable oil.

The method for preparing the contrast agent according to the present disclosure includes a step of preparing an iodinated unsaturated fatty acid ethyl ester by subjecting the unsaturated fatty acid ethyl ester to an iodination reaction. The iodination reaction is performed by adding gaseous hydrogen iodide (HI) to the unsaturated fatty acid ethyl ester. As shown in Reaction Formula 1 below, the gaseous hydrogen iodide (HI (g)) is prepared by allowing red phosphorus and particulate iodine to react with distilled water.

$3I_2+2P+6H_2O \rightarrow 2PI_3+6H_2O \rightarrow 6HI(g)+2H_3PO_3$ <Reaction Formula 1>

When gaseous hydrogen iodide and the unsaturated fatty acid ethyl ester are allowed to react at room temperature using the property of the gaseous hydrogen halide bonds well to a carbon double bond, an iodinated unsaturated fatty acid ethyl ester is synthesized.

The method for preparing the contrast agent according to the present disclosure includes first purification with a base and second purification with silica gel, after the iodination reaction. As shown in Reaction Formula 2 below, hydrogen iodide (HI (g)) remaining unreacted after the iodination reaction produces free iodine ($I_2$) due to ultraviolet light and oxygen. Since the free iodine causes browning, it needs to be removed.

$4I^-+O_2+4H^+ \rightarrow 2I_2+2H_2O$ <Reaction Formula 2>

In order to remove the free iodine, first purification with a base is performed. When the free iodine is treated with the base, it is removed according to the reaction shown in Reaction Formula 3 below. The base may be sodium hydroxide, potassium hydroxide, calcium hydroxide, barium hydroxide, or ammonium hydroxide, but is not limited thereto. Preferably, the base may be potassium hydroxide.

However, iodine ions ($I^-$) may be generated again, and the iodine ions may be converted back to free iodine according to Reaction Formula 2 above.

$I_2+2OH^- \rightarrow I^-+IO^-+H_2O$ <Reaction Formula 3>

For this reason, after the first purification with the base, second purification for removing iodine ions is required. After the first purification is performed, the second purification is performed using silica gel that is used to remove polar substances. After the secondary purification is performed, the purification product shows a color similar to that of Lipiodol. The iodination reaction and the purification process will be described in detail in the following examples.

The method for preparing the contrast agent according to the present disclosure includes a step of adding a non-iodinated unsaturated fatty acid ethyl ester and sulfur dioxide ($SO_2$) to the iodinated unsaturated fatty acid ethyl ester.

In the contrast agent of the present disclosure, the roles of the non-iodinated unsaturated fatty acid ethyl ester and sulfur dioxide ($SO_2$) are as described above.

Hereinafter, the present disclosure will be described in more detail with reference to examples. However, the following examples are for illustrative purposes, and the scope of the present disclosure is not limited thereto.

EXAMPLE 1

Selection of Vegetable Oils as Substitute for Poppy Seed Oil

Poppy seed oil has a saturated fat content of 13.5%, a mono-unsaturated fat content of 19.7%, and a poly-unsaturated fat content of 62.4%, and thus the unsaturated fatty acid content thereof is higher than the saturated fatty acid content. Referring to FIG. 1, soybean oil and sunflower seed oil having a composition similar to that of poppy seed oil were selected. The compositions of the selected oils are shown in Table 1 below.

TABLE 1

|  | Saturated fats | Mono-unsaturated fats | Poly-unsaturated fats |
| --- | --- | --- | --- |
| Poppy seed oil | 13.5% | 19.7% | 62.4% |
| Sunflower seed oil | 13.0% | 18.5% | 68.5% |
| Soybean oil | 15.2% | 22.8% | 60.9% |

EXAMPLE 2

Preparation of Iodinated Unsaturated Fatty Acid Ethyl Ester

1. Preparatin of Unsaturated Fatty Acid Ethyl Ester by Transesterification

In order to modify each vegetable oil into a structure similar to Lipiodol, a transesterification reaction was performed. 200 g of each of the vegetable oils (sunflower seed oil and soybean oil) was placed in a 1-L round bottom flask, and 180 g of ethanol (90 wt % based on the oil) and 2 g of solid KOH (1 wt % based on the oil) as a base catalyst were added thereto. Since saponification could occur in the presence of water, the reaction was performed in a water-free state. The transesterification reaction was performed by stirring for 2 hours at a temperature of 75 to 80° C., thus preparing esterified oils (transesterified sunflower seed oil (TSS oil) and transesterified soybean oil (TS oil)). The prepared TSS oil and TS oil were sufficiently cooled to a temperature of 40° C. or less, and then triple distilled water was added thereto in an amount of 1.5 to 2 times the mass (200 g) of each vegetable oil used in the start of the reaction, and each of the oils was washed for 2 hours. Thereafter, the supernatant (oil layer) was collected using a separatory funnel, and the paraffin-type saturated fatty acid ethyl ester floating in the oil was removed using a Buchner funnel combined with a vacuum filter. The reaction process is shown in FIG. 1.

Figure 2:
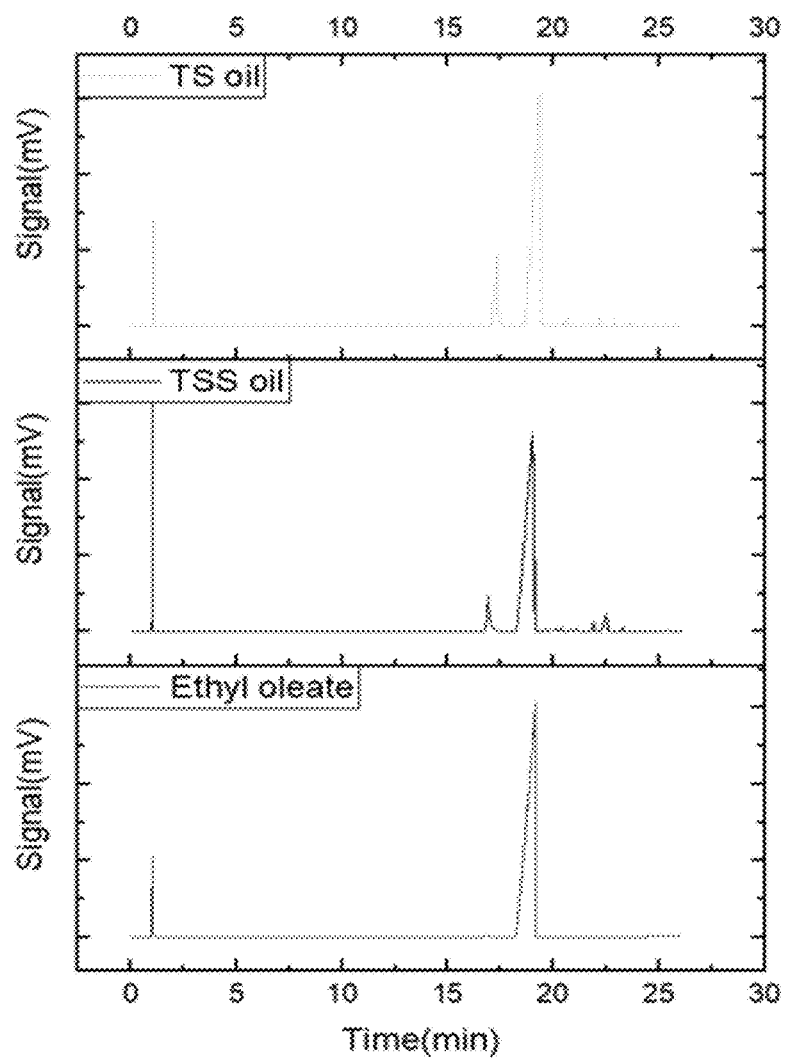
FIG. 2 shows chromatograms obtained by analyzing TS oil, TSS oil and ethyl oleate by GC.

In order to confirm whether the main component of each of the products (TSS oil and TS oil) was ethyl oleate, each of the products was analyzed using a GC (GC-6500GC, Youngin Chromass) equipped with a flame ionization detector (FID), and the results of the analysis are shown in FIG. 2. Thereby, it was confirmed that the main component of each of the products was ethyl oleate.

2. Iodination of Fatty Acid Ethyl Ester

Figure 3:
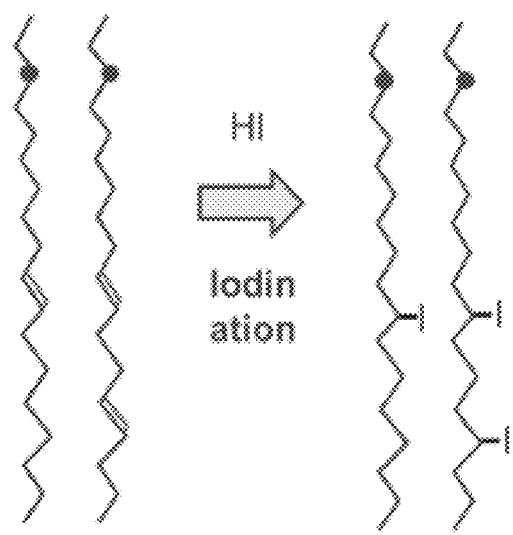
FIG. 3 is a conceptual view showing a method of performing an iodination reaction on TSS/TS oil.

In order to add the contrast material iodine to the synthesized TSS or TS oil, gaseous hydrogen iodide was synthesized and added to the synthesized oils. A mixture of 150 g of solid-state iodine and 30 g of powdery red phosphorus was placed in one side of each of two prepared jacketed round bottom flasks, and the TSS or TS oil was placed in the other side. Hydrogen iodide was synthesized by introducing triple distilled water into the side containing the mixture of red phosphorus and hydrogen iodide. The synthesized gaseous hydrogen iodide was allowed to react with the TSS or TS oil for 24 hours. FIG. 3 shows an example of the chemical structure of the unsaturated fatty acid ethyl ester iodinated according to the above-described reaction process.

Since the synthesized oils were highly viscous, each of the oils was diluted with ethanol and a purification reaction was performed. Ethanol was added to each of the synthesized oils in an amount twice the mass of each synthesized oil and each oil was sufficiently diluted with the ethanol for 1 hour, and then 0.5 M KOH was added in an amount twice the mass of each oil and allowed to react for 3 hours. After the reaction, only the oil layers were separated using a separatory funnel. In addition, the separated oils were diluted with ether and allowed to react with 0.1M sodium thiosulfate ($Na_2S_2O_3$), and this process was repeated 2 to 3 times. The purified oil layers were separated again using a separatory funnel, and dried with a sufficient amount of magnesium sulfate to remove water. Thereafter, the magnesium sulfate was removed using a 0.2-μm membrane filter, thus preparing iodinated sunflower seed (ISS) oil and iodinated soybean (IS) oil as final products.

EXAMPLE 3

Analysis of ISS and IS Oils

1. Analysis of Physical Properties
1) Analysis of Density

Figure 4:
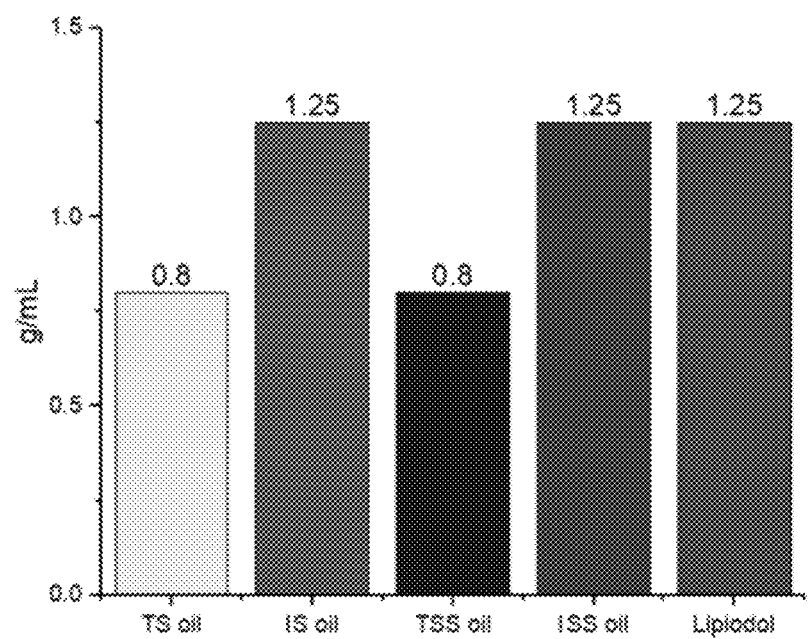
FIG. 4 is a graph comparing the densities Lipiodol, TS oil, IS oil, TSS oil and ISS oil.

As iodine is added to each of the oils, the physical composition of the oil changes and the density thereof changes accordingly. It was found that the density of Lipiodol was 1.25 g/ml (FDA: 3475622), and whether the densities of the ISS and IS oils are similar to that of Lipiodol was checked. The density of each of the oils was determined by measuring the exact volume (2 ml), and the results of the measurement are shown in FIG. 4. As a result of the measurement, the densities of the TSS and TS oils were measured to be 0.8 g/ml, and the densities of the ISS and IS oils were measured to be 1.25 g/ml, which were equal to the density of Lipiodol.

2) Analysis of Viscosity

Figure 5:
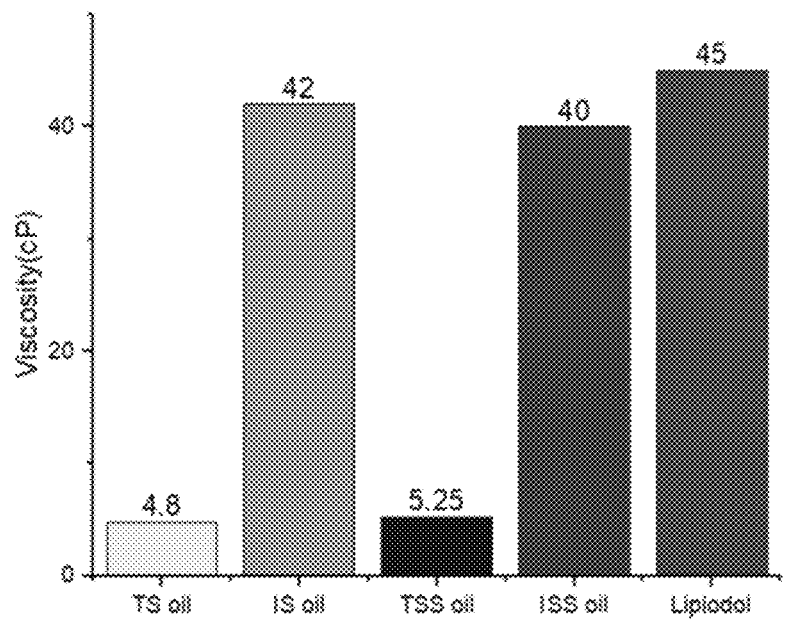
FIG. 5 is a graph comparing the viscosities of Lipiodol, TS oil, IS oil, TSS oil and ISS oil.

As iodine is added to each of the oils, the intermolecular interaction in the oil increases, resulting in an increase in the viscosity of the oil. Therefore, whether the viscosities of the ISS and IS oils are similar to the viscosity of Lipiodol was checked. The viscosities were measured using a viscometer (SP-100) at room temperature, and the results of the measurement are shown in FIG. 5.

As a result of the measurement, it was confirmed that the viscosities were 4.8 cP for the TS oil, 5.25 cP for the TSS oil, 42 cP for the IS oil, 40 cP for the ISS oil, and 45 cP for Lipiodol, indicating that the viscosities of the ISS and IS oils were similar to that of Lipiodol.

Therefore, the ISS and IS oils having densities and viscosities similar to those of Lipiodol were successfully synthesized, and thus were predicted to have the same composition and structure as those of Lipiodol.

2. Analysis of Chemical Structure
1) $^1$H-NMR Analysis

Figure 6:
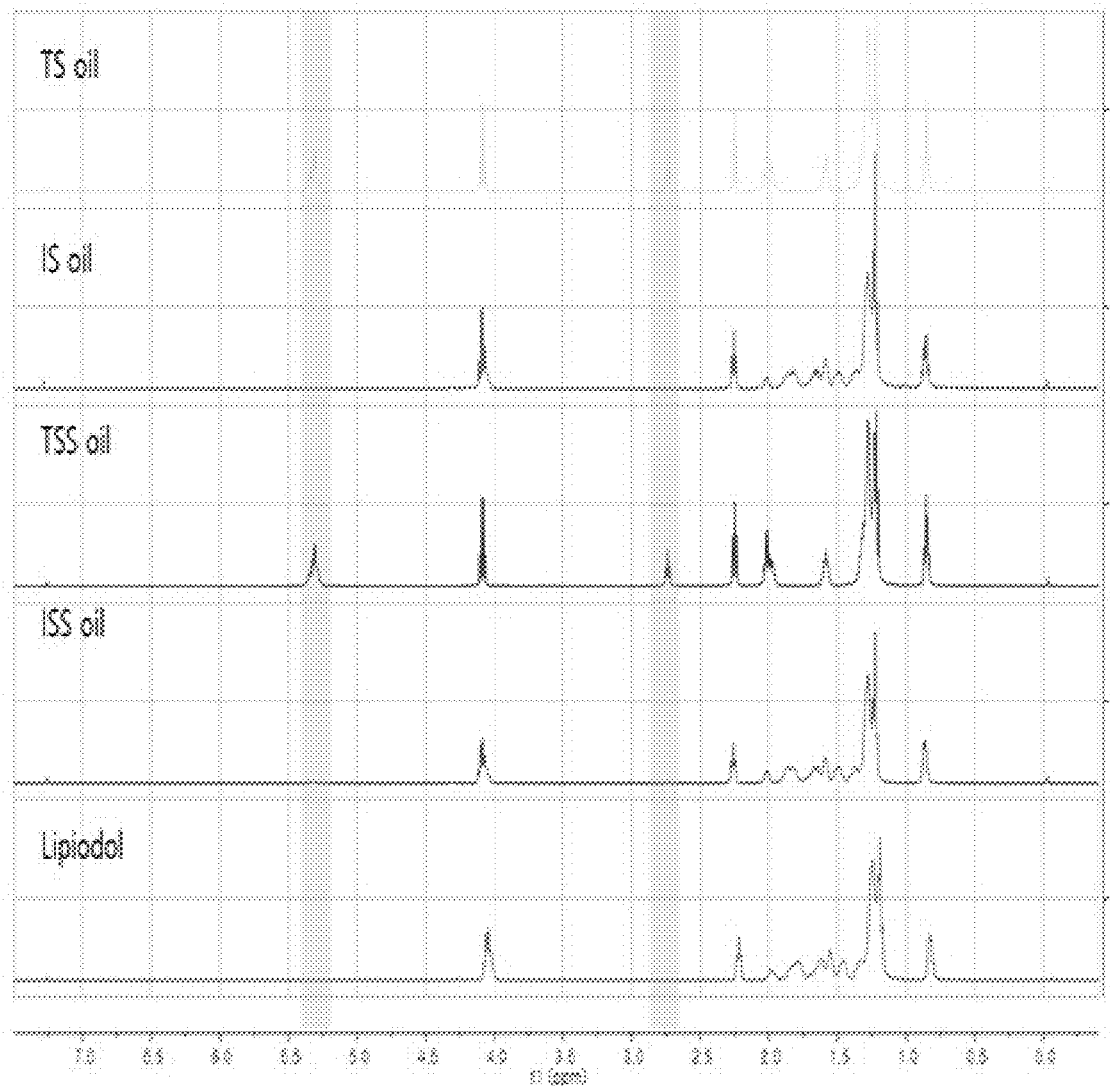
FIG. 6 shows the results of analyzing the structures of Lipiodol, TS oil, IS oil, TSS oil and ISS oil by $^1$H-NMR.

A crucial structural difference between before and after the iodination reaction is that a carbon-iodine bond is formed by the addition of iodine to a carbon-carbon double bond. In order to confirm this difference, analysis was performed by $^1$H-NMR (Bruker, Avance II500). 100 μl of each measurement sample was mixed with 1000 μl of $CDCl_3$ and analyzed by $^1$H-NMR, and the results of the analysis are shown in FIG. 6. The peak corresponding to the carbon-iodine bond appeared at 2.2 ppm. However, it was difficult to confirm because it was widely spread by hydrogen bonded to many carbons. The peak of the carbon-carbon double bond appeared at 2.8 ppm and 5.35 ppm. It was confirmed that, after iodination, the peaks at 2.8 ppm and 5.35 ppm corresponding to the double bond peak disappeared, and the peak at 2 ppm changed. In particular, it was confirmed that the structure of the ISS oil was 99% similar to the structure of Lipiodol.

2) FT-IR (ATR) Analysis

Figure 7:
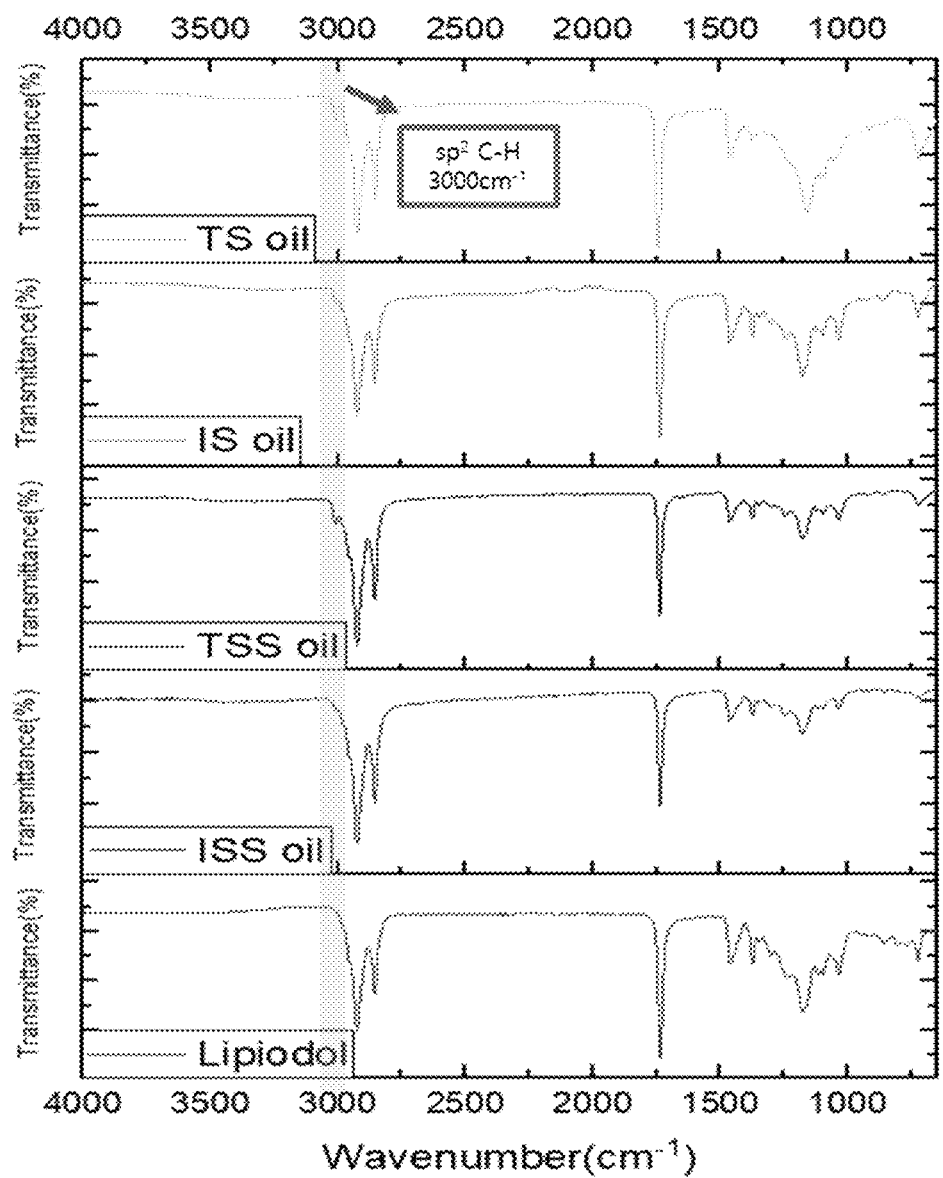
FIG. 7 shows FT-IR spectra of Lipiodol, TS oil, IS oil, TSS oil and ISS oil.

Analysis was performed using FT-IR (Perkin-Elmer, spectrum-1000). Liquid samples were measured in ATR mode. After placing each sample on a lens, the transmittance in the range of 4000 to 650 $cm^{-1}$ was measured to determine the presence or absence of a carbon-carbon double bond. The results of the analysis are shown in FIG. 7. It was confirmed that the $sp^2$ carbon-hydrogen bond peak corresponding to 3100 $cm^{-1}$ disappeared following iodination. In addition, it was confirmed that the structures of the ISS and IS oils were similar to the structure of Lipiodol.

3) GC Analysis

Figure 8:
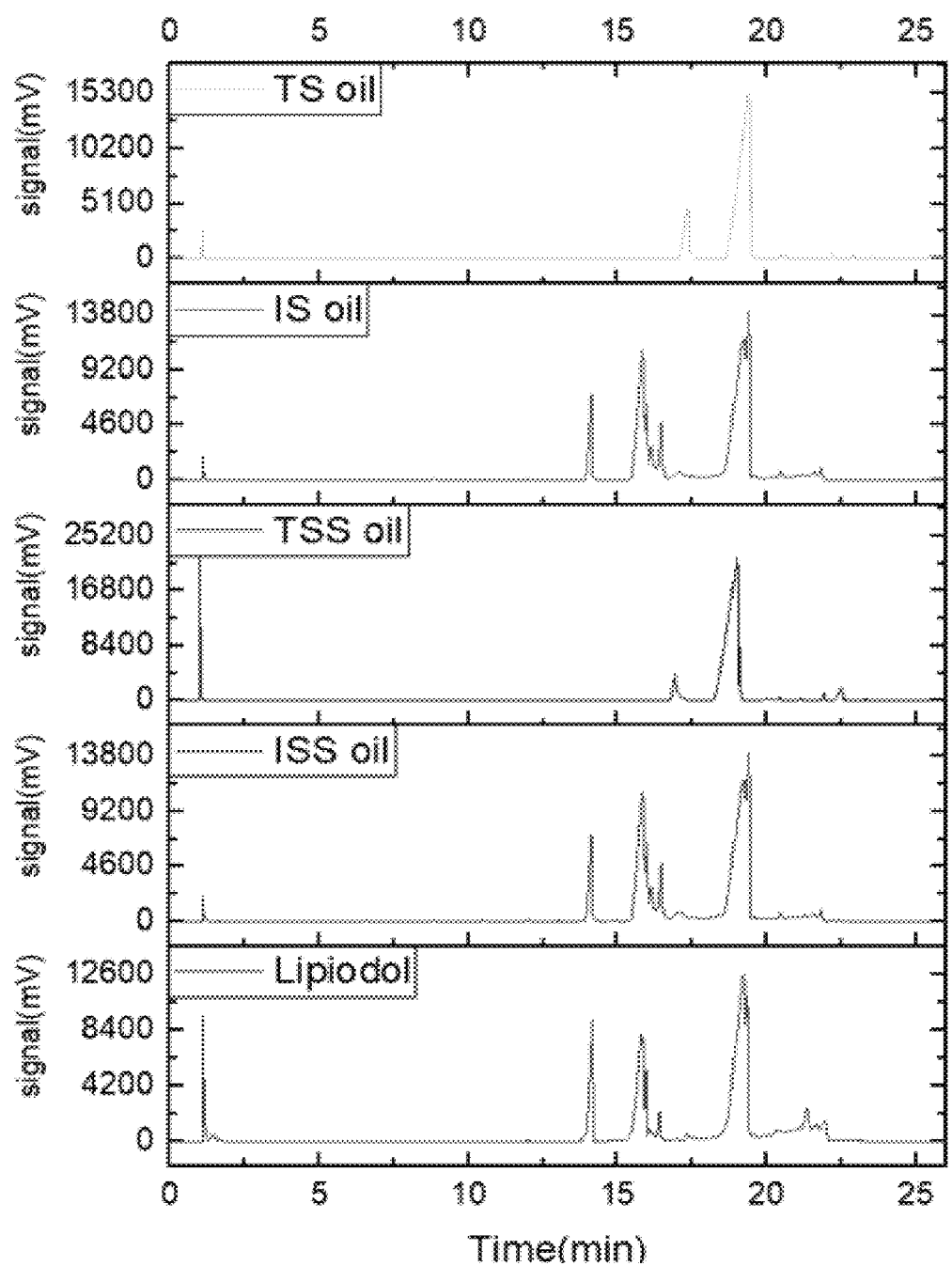
FIG. 8 shows chromatograms obtained by analyzing the structures of Lipiodol, TS oil, IS oil, TSS oil and ISS oil by GC.

Analysis was performed using a GC (GC-6500GC, Youngin Chromass) equipped with an FID detector. The content of iodine in each of the TSS and TS oils was calculated as an integral ratio and analyzed, and the results are shown in FIG. 8. The peak at the retention time of 16 minutes was stearic acid ethyl ester. This peak likewise appeared in the TSS and ISS oils. The reason is that the peak corresponded to a saturated hydrocarbon that did not undergo the reaction. The amount of iodine added was calculated based on the change in the peak at 18 to 19 minutes corresponding to ethyl oleate. The integral value of the peak at 18 minutes for the TSS oil was 75,400, and the integral value between 18 minutes and 22 minutes in the ISS oil was 296,000. It was confirmed that the peak of ethyl oleate moved 38%, 35% of iodine was added to the ISS oil.

EXAMPLE 4

Purification of Iodine Remaining after Iodination Reaction

Purification was attempted in various ways in order to remove iodine remaining after the iodination reaction. Optimization of purification was performed with the ISS oil, and iodine remaining after purification was confirmed using a free iodine test and a UV-VIS spectrophotometer.

In the free iodine test for determining the content of $I_2$, 5 ml of chloroform was added to and diluted in 2 g of the ISS oil, and then a 5% solution of KI was prepared and added thereto. Thereafter, 1 wt % of a starch indicator and whether a purple layer was sufficiently formed was checked. In addition, the absorbance at 420 nm and 460 nm was measured using a UV-VIS spectrophotometer (Biochrom, Libra S70).

1. Purification with Potassium Hydroxide

Figures 9, 10:
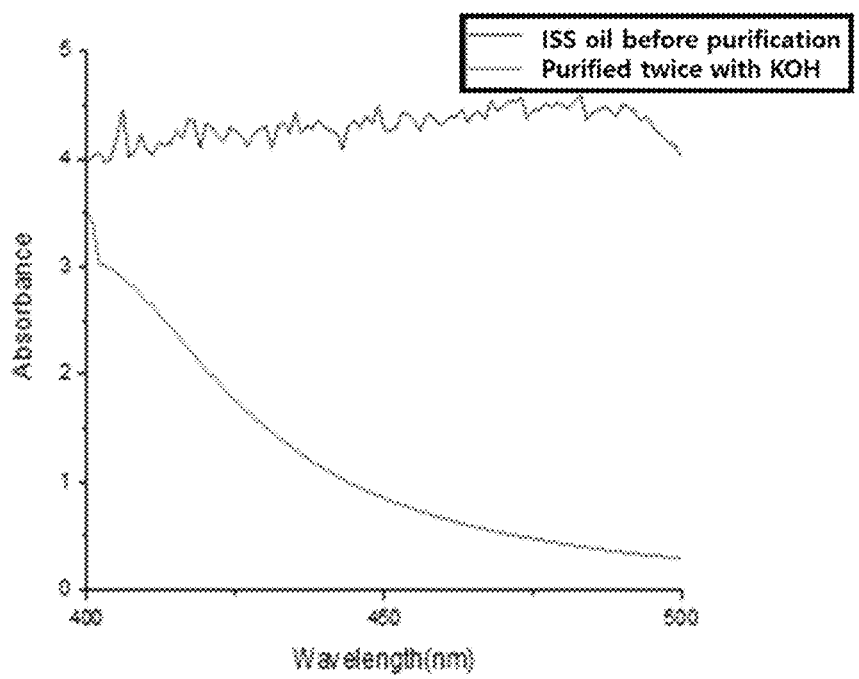
FIG. 9 shows the results of measuring the absorbance values of ISS oil before purification and ISS oil after purification with potassium hydroxide by a UV-Vis spectrophotometer.
FIG. 10 shows the results of observing the color change over time after purifying ISS oil with potassium hydroxide.

The ISS oil was diluted sufficiently with ethanol and purified 2 to 3 times with 0.5 M potassium hydroxide to remove the remaining iodine ions and iodine. After purification, the remaining iodine was confirmed using a free iodine test and a UV-VIS spectrometer. The results of the free iodine test indicated that the content of iodine in the ISS oil was an average of 0.1 wt %, which was twice as high as that of Lipiodol (0.05 wt %). The absorbance value measured by the UV-VIS spectrophotometer was higher than that of Lipiodol. The measured values of absorbance before and after purification are shown in FIG. 9. The synthesized material was discolored between one week and one month and did not maintain its stability. The results are shown in FIG. 10.

2. Purification with Sodium Thiosulfate

Figure 11:
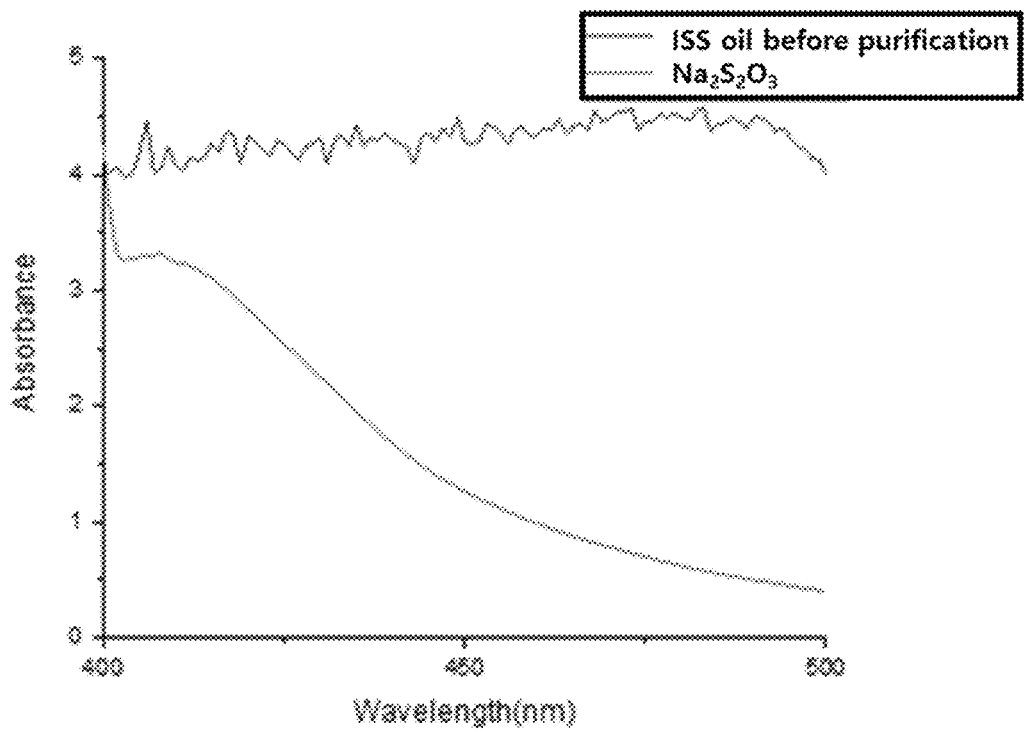
FIG. 11 shows the results of measuring the absorbance values of ISS oil before purification and the absorbance values of ISS oil after purification with sodium thiosulfate ($Na_2S_2O_3$) by a UV-Vis spectrophotometer.
Figure 12:
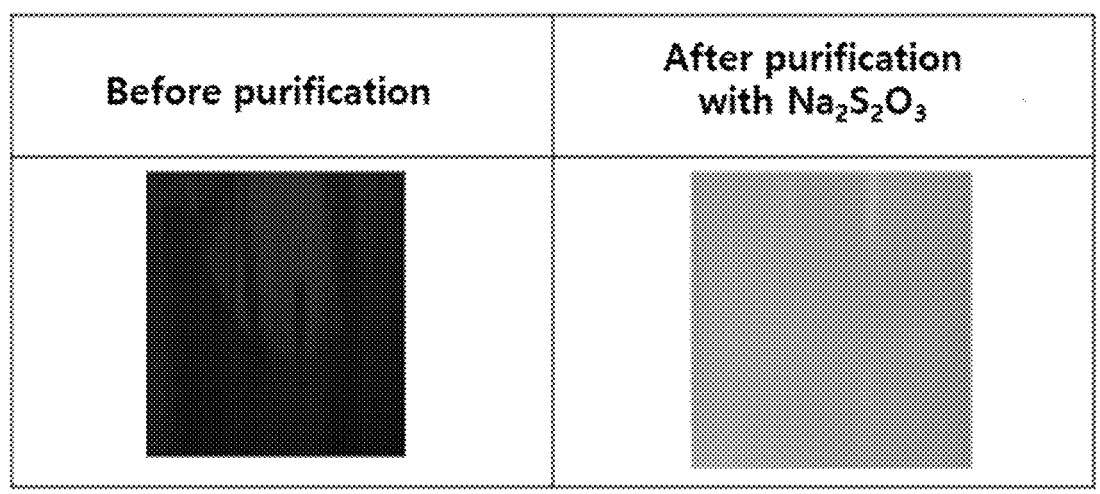
FIG. 12 shows the results of comparing the color of ISS oil between before and after purification with sodium thiosulfate ($Na_2S_2O_3$).

It was confirmed that, when purification with 0.1 M sodium thiosulfate ($Na_2S_2O_3$) was performed, iodine was effectively removed. The absorbance values before and after purification are shown in FIG. 11, and the color change between before and after purification is shown in FIG. 12. However, as a result of the free iodine test, it was confirmed that the iodine content was 0.1 wt %, which was similar to that in the case of purification with potassium hydroxide, and browning appeared within one month. For this reason, it was determined that additional purification after purification with potassium hydroxide or sodium thiosulfate ($Na_2S_2O_3$) was necessary, and thus additional purification was performed.

3. Purification with Ion Exchange Resin

Figure 13:
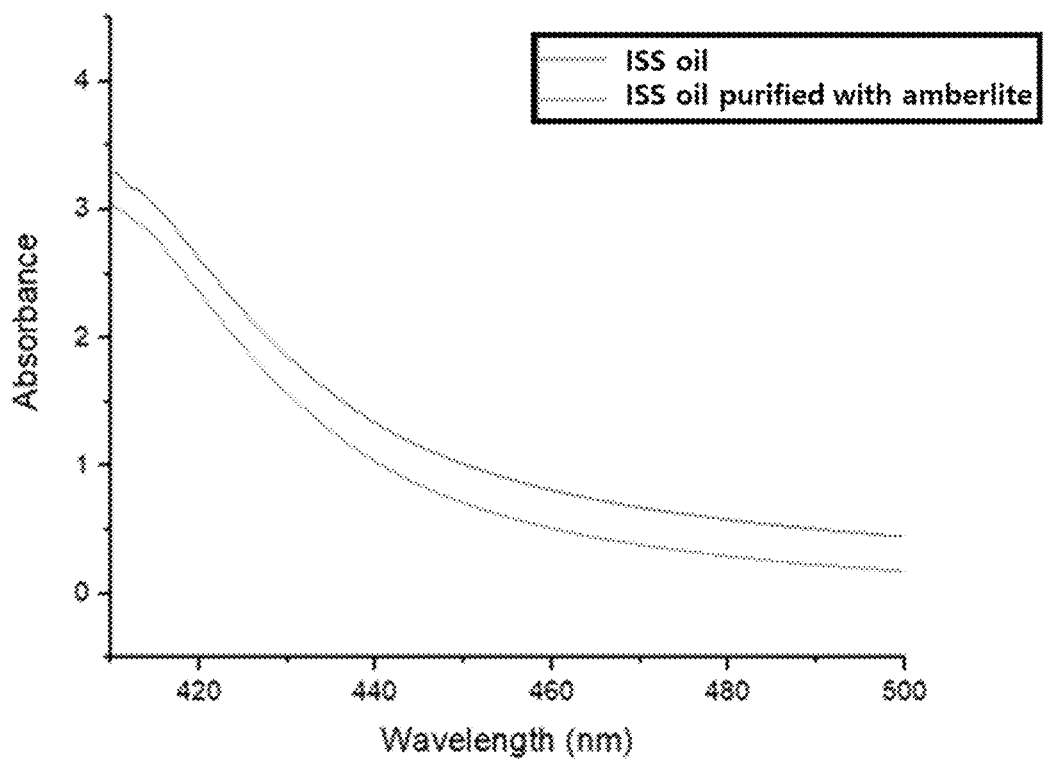
FIG. 13 is a graph showing the results of measuring the absorbance values of ISS oil, subjected to first purification with potassium hydroxide, and ISS oil (ISS oil purified with amberlite), subjected to second purification with ion exchange resin after first purification, by a UV-Vis spectrophotometer.
Figure 14:
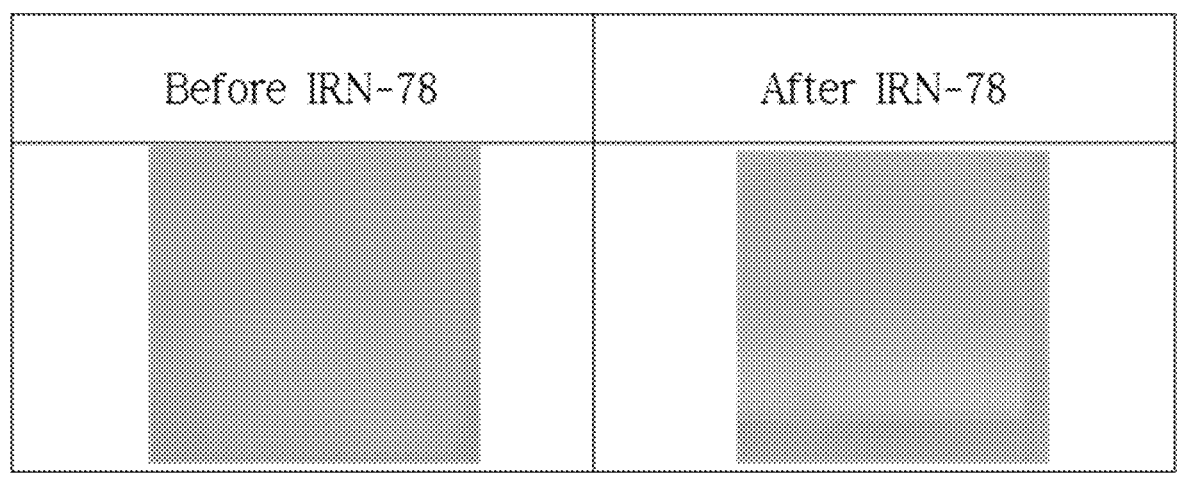
FIG. 14 shows the results of comparing the color between ISS oil (Before IRN-78), subjected to first purification with potassium hydroxide, and ISS (After IRN-78) subjected to second purification with ion exchange resin after first purification.

First, after purification with potassium hydroxide or sodium thiosulfate ($Na_2S_2O_3$), the product was passed through an ion exchange resin. Amberlite IRN-78 was used as the ion exchange resin. This resin is an anion exchange resin expected to effectively adsorb and exchange iodine ions. When the product was passed once through the ion exchange resin, there was no problem, but when the product was passed two or more times, there was a problem in that the pH increased due to excessive dissolution of the ammonium ions of the resin. The absorbance values before and after purification were measured and the results are shown in FIG. 13. The results of measuring the color change between before and after purification are shown in FIG. 14. As a result of the free iodine test, it was confirmed that 0.07 wt % of iodine was contained in the oil. This iodine content was also higher than that of Lipiodol. Even after purification through the ion exchange resin, browning occurred, and the polystyrene-based resin gradually dissolved in the oil, and thus this purification method showed limitations.

4. Purification with Silica Gel

Figures 15, 16:
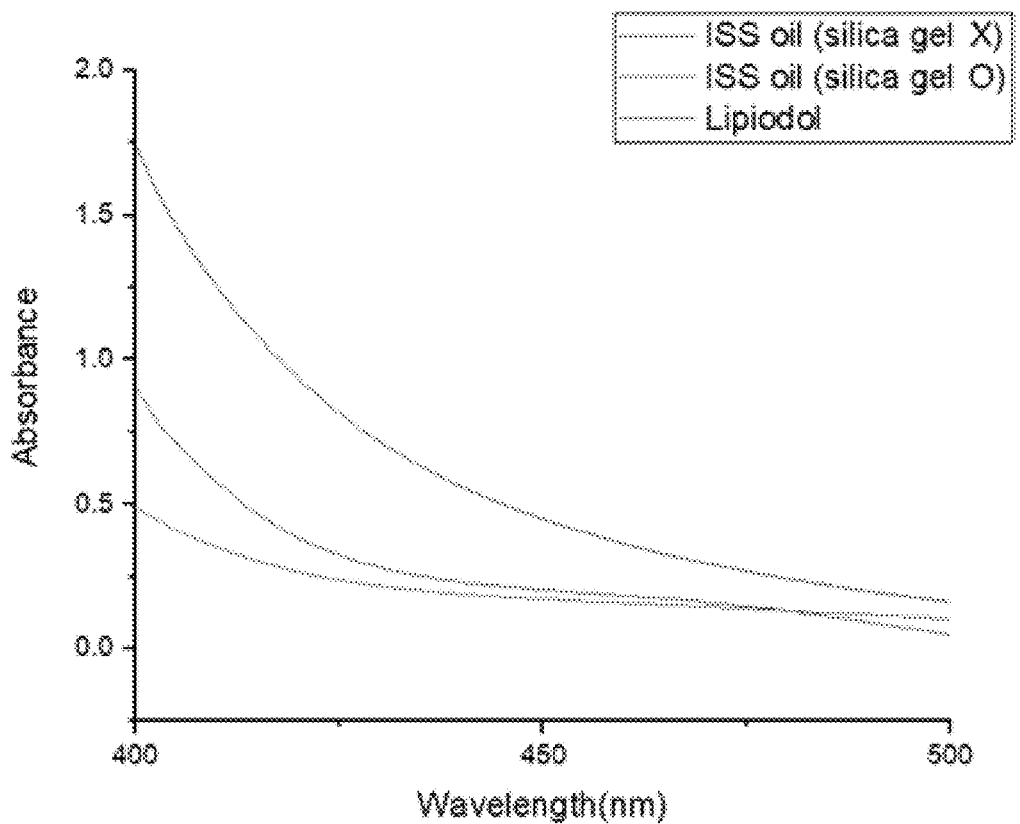
FIG. 15 is a graph showing the results of measuring the absorbance values of ISS oil (Silica gel X) subjected to first purification with potassium hydroxide, ISS oil (Silica gel O) subjected to second purification with silica gel after first purification, and Lipiodol, by a UV-Vis spectrophotometer.
FIG. 16 shows the results of comparing the color between ISS oil immediately after synthesis, ISS oil (Silica gel X) subjected to first purification with potassium hydroxide, and ISS oil (Silica gel O) subjected to second purification with silica gel after first purification.

First, after purification with potassium hydroxide or sodium thiosulfate ($Na_2S_2O_3$), the product was passed through silica gel (ZEO CHEM silica gel, ZEO prep 60 Å). The absorbance values before and after purification with silica gel are shown in FIG. 15, and the color change between before and after purification is shown in FIG. 16. After purification with silica gel, the oil had a color similar to that of Lipiodol, and the absorbance value thereof was measured to be similar to that of Lipiodol. However, even after purification with silica gel, browning occurred within one month.

EXAMPLE 5

Treatment with Stabilizer

To solve the above-described problem, a stabilizer was added after purification. The TSS oil, which is a product obtained before the iodination reaction, was added in view of the highly reactive property of iodine ions, and sulfur dioxide, an anion inhibitor, was added to prevent iodine from being ionized. The additive was prepared by adding 1 wt % of sulfur dioxide to the TSS oil.

Figure 17:
FIG. 17 shows the results of observing the color change for 3 weeks after ISS oil subjected to second purification with silica gel after first purification with potassium hydroxide was treated with various concentrations (0, 0.5, 1, and 2 wt %) of sulfur dioxide-containing TSS oil (TSS oil/$SO_2$, prepared by adding 1 wt % of sulfur dioxide to TSS oil).
Figure 18A:
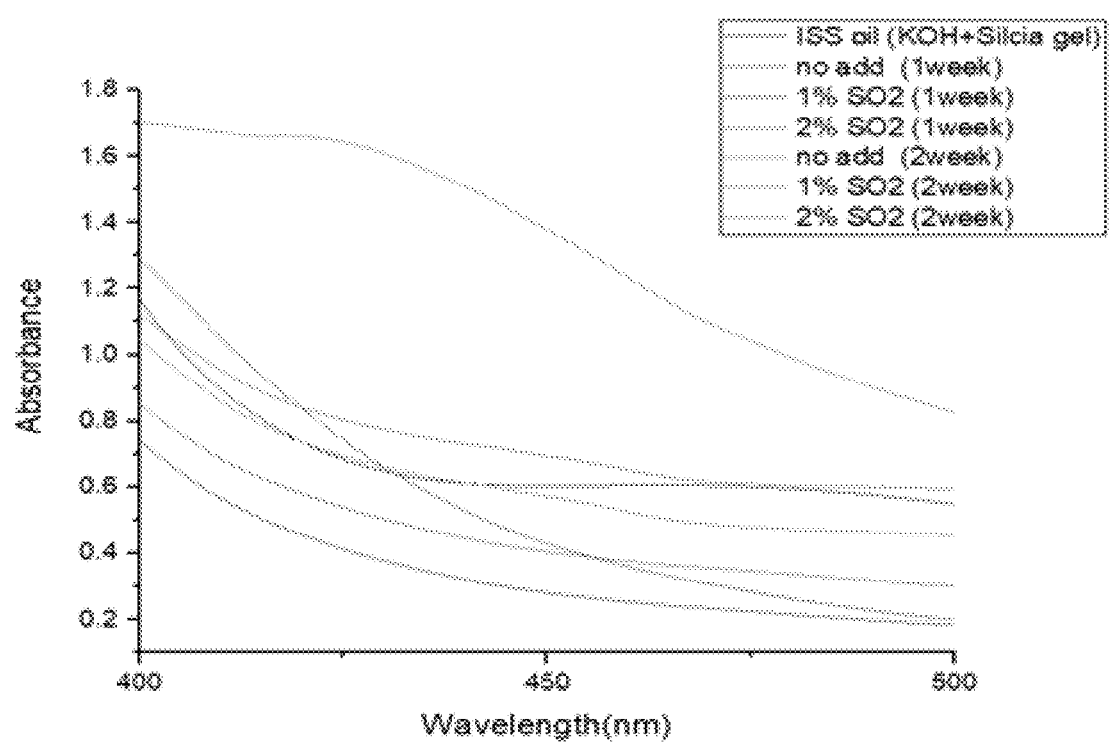
FIG. 18A is a graph showing the results of measuring absorbance by a UV-VIS spectrophotometer for 2 weeks after ISS oil subjected to second purification with silica gel after first purification with potassium hydroxide was treated with various concentrations (0, 1 and 2 wt %) of sulfur dioxide-containing TSS oil (TSS oil/$SO_2$, prepared by adding 1 wt % of sulfur dioxide to TSS oil).
Figure 18B:
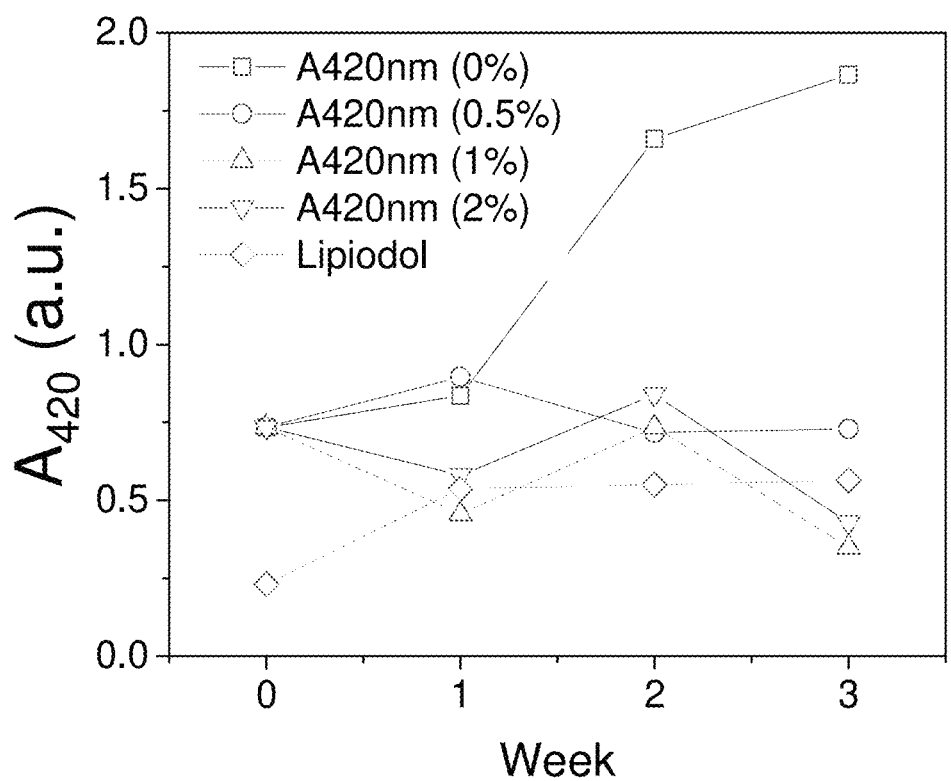
FIG. 18B is a graph showing the results of measuring the absorbance at 420 nm for 3 weeks for samples obtained by treating ISS oil, subjected to second purification with silica gel after first purification with potassium hydroxide, with various concentrations (0, 0.5, 1 and 2 wt %) of sulfur dioxide-containing TSS oil (TSS oil/$SO_2$, prepared by adding 1 wt % of sulfur dioxide to TSS oil), and Lipiodol.
Figure 18C:
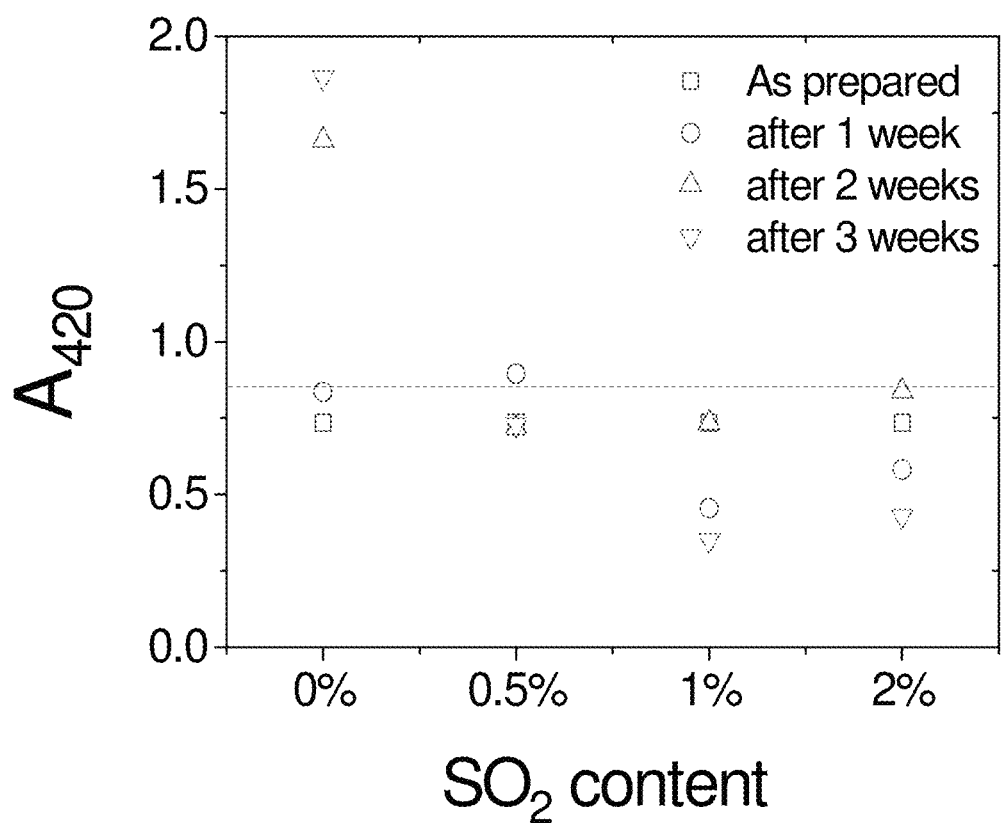
FIG. 18C is a graph obtained by converting the x-axis of FIG. 18B into the concentration of sulfur dioxide.
Figure 19:
FIG. 19 shows the results of observing the color change for 3 weeks after ISS oil subjected to second purification with silica gel after first purification with sodium thiosulfate ($Na_2S_2O_3$) was treated with various concentrations (0.5, 1, 1.5 and 2 wt %) of sulfur dioxide-containing TSS oil (TSS oil/$SO_2$, prepared by adding 1 wt % of sulfur dioxide to TSS oil).
Figure 20:
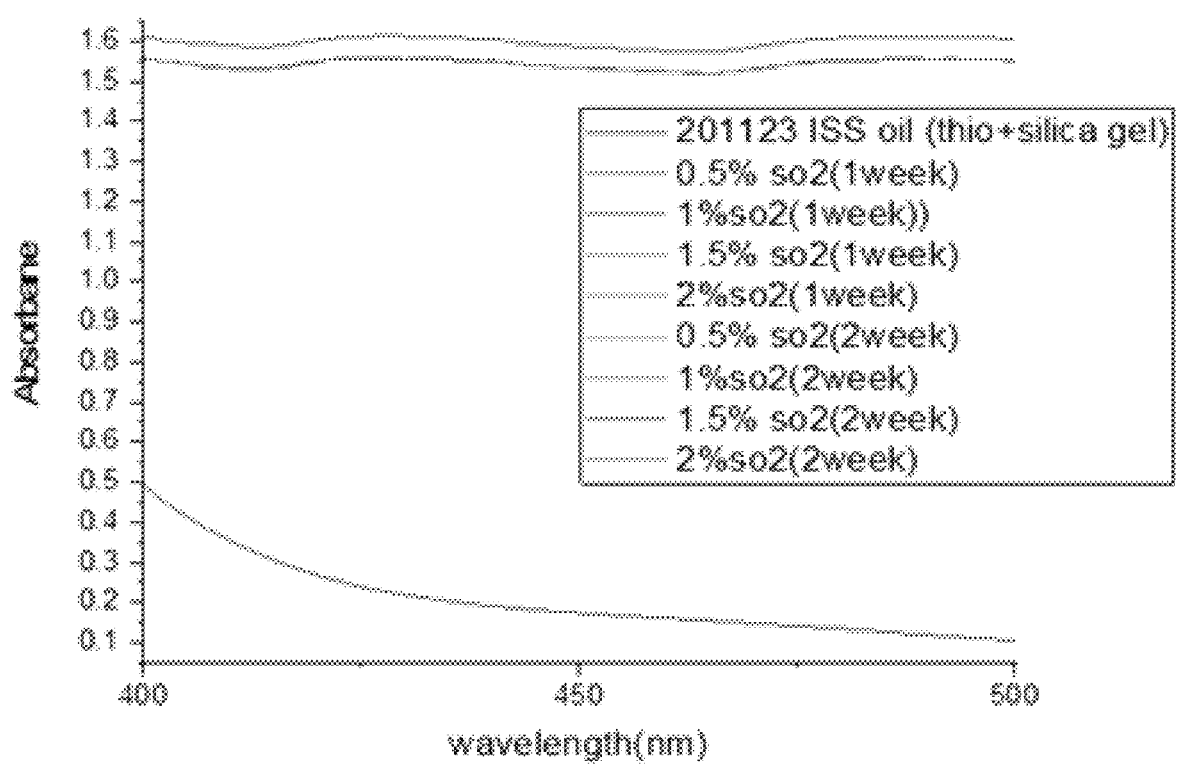
FIG. 20 shows the results of measuring absorbance by a UV-Vis spectrophotometer for 3 weeks after ISS oil subjected to second purification with silica gel after first purification with sodium thiosulfate ($Na_2S_2O_3$) was treated with various concentrations (0.5, 1, 1.5 and 2 wt %) of sulfur dioxide-containing TSS oil (TSS oil/$SO_2$, prepared by adding 1 wt % of sulfur dioxide to TSS oil).

After first purification with potassium hydroxide or sodium thiosulfate ($Na_2S_2O_3$), second purification with silica gel was performed, and the additive was added to the ISS oil in amounts of 0.5, 1 and 2 wt %. Then, the color change of the ISS oil was observed under a fluorescent lamp for 3 weeks, and the absorbance was measured. The results of observing the color change after treatment with the additive following first purification with potassium hydroxide and second purification with silica gel are shown in FIG. 17. The results of measuring the absorbance for 2 weeks are shown in FIG. 18A, and the results of measuring the absorbance for 3 weeks are shown in FIGS. 18B and 18C. The results of observing the color change after treatment with the additive following first purification with sodium thiosulfate ($Na_2S_2O_3$) and second purification with silica gel are shown in FIG. 19, and the results of measuring the absorbance for 2 weeks are shown in FIG. 20. As a result, it was confirmed that the method comprising first purification with potassium hydroxide showed higher stability.

Figures 21, 22:
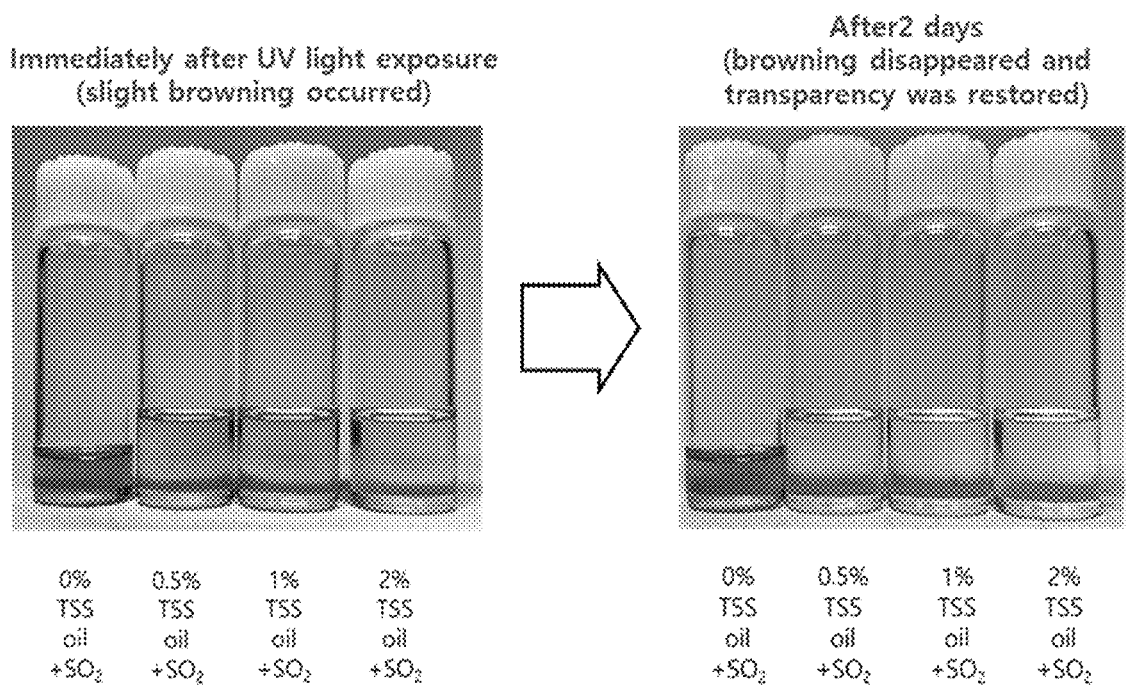
FIG. 21 shows the results of observing the color change 2 days after inducing browning by exposure to UV light after ISS oil subjected to second purification with silica gel after first purification with potassium hydroxide was treated with various concentrations (0.5, 1, 1.5 and 2 wt %) of sulfur dioxide-containing TSS oil (TSS oil/$SO_2$, prepared by adding 1 wt % of sulfur dioxide to TSS oil) and left to stand for 3 weeks.
FIG. 22 shows the results of comparing the X-ray contrast rates of TSS oil, ISS oil, and Lipiodol.

In addition, it was confirmed that, even when browning was forcibly induced by exposure to strong ultraviolet light after 3 weeks, the browning disappeared after 2 days and the transparency was restored. The results are shown in FIG. 21.

EXAMPLE 6

Test for Contrast Agent Effect

1. Test for Contrast Effect by Micro-CT

Whether the ISS oil is impermeable to X-rays was examined using micro-CT (Bruker, Skyscan-100), and the results are shown in FIG. 22. It was confirmed that the contrast rate of the ISS oil was about 90% of the contrast rate of Lipiodol, indicating that the contrast rate of the ISS oil is similar to that of Lipiodol.

2. Cytotoxicity Test

A cytotoxicity test was performed by UMUST R&D Corp. In vitro toxicity evaluation of the ISS and IS oils and Lipiodol was performed using fibroblasts (L-929).

The test was conducted in compliance with ISO 10993: 2009, Biological Evaluation of Medical Devices-Part 5: Tests for in vitro Cytotoxicity, 9.2 test on extracts UPS39: 2016 <87>Biological reactivity test in vitro Elution test, and Ministry of Food and Drug Safety Notification No. 2019-4:2019, Common standards for biological safety of medical devices. MEM medium was used as an elution solvent. For elution, the synthesized material (ISS oil, Lipiodol, or TSS oil) was diluted at 1:50 in 70% ethanol containing 0.1% sodium hydroxide, and then diluted at 0.00001, 0.0001, and 0.001.

Figure 23:
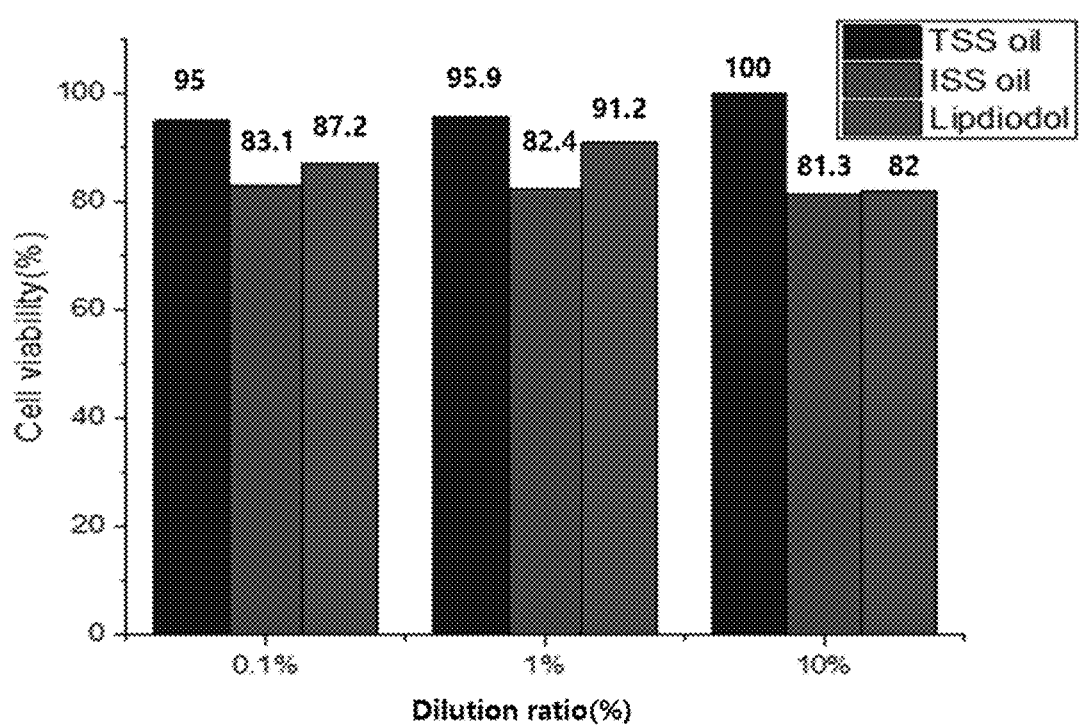
FIG. 23 is a graph showing the cytotoxicities of TSS oil, ISS oil and Lipiodol to fibroblasts (L-929).

$1\times10^4$ fibroblasts were seeded into each well, and then treated and incubated with the diluted synthesized material for 24 hours. Then, the cytotoxicity of the diluted synthesized material was analyzed by XTT, and the results are shown in FIG. 23. As a result of the cytotoxicity test, it was confirmed that the ISS oil showed cytotoxicity similar to that of Lipiodol.

As described above, the physical properties (density and viscosity) and chemical structure of the iodinated fatty acid ethyl ester derived from vegetable oil, which is contained as a main component in the contrast agent of the present disclosure, were similar to those of Lipiodol, and the cytotoxicity thereof was also measured to be similar to that of Lipiodol, and the contrast rate thereof was also measured to be similar to that of Lipiodol. Thus, it was confirmed that the iodinated fatty acid ethyl ester is sufficient to replace the conventional Lipiodol contrast agent. In addition, it was confirmed that, since the contrast agent of the present disclosure contained the non-iodinated unsaturated fatty acid ethyl ester and sulfur dioxide ($SO_2$), it did not undergo browning for a considerable period of time and maintained the same transparency as that upon initial production. Thus, instability problems such as browning caused by the release of iodine (bound to the iodine-based contrast agent) from the contrast agent have been effectively solved according to the present disclosure.

The effects of the present disclosure are not limited to the above-mentioned effects. It is to be understood that the effects of the present disclosure include all effects that may be deduced from the features described in the above description and the appended claims.

The above description of the present disclosure is exemplary, and those of ordinary skill in the art will appreciate that the present disclosure may be easily modified into other specific forms without departing from the technical spirit or essential characteristics of the present disclosure. Therefore, it should be understood that the exemplary embodiments described above are exemplary in all aspects and are not restrictive. For example, each component described to be of a single type may be implemented in a distributed manner. Likewise, components described to be distributed may be implemented in a combined manner.

The scope of the present disclosure is defined by the following claims. It shall be understood that all modifications and embodiments conceived from the meaning and scope of the claims and equivalents thereto are included within the scope of the present disclosure.

What is claimed is:

1. A method for preparing a contrast agent, the method comprising:
   preparing an unsaturated fatty acid ethyl ester from vegetable oil by a transesterification reaction;
   preparing an iodinated unsaturated fatty acid ethyl ester by subjecting the unsaturated fatty acid ethyl ester to an iodination reaction;
   first purifying the iodinated unsaturated fatty acid ethyl ester with at least one base selected from the group consisting of sodium hydroxide, potassium hydroxide, calcium hydroxide, barium hydroxide, sodium thiosulfate, and ammonium hydroxide, and then second purifying the iodinated unsaturated fatty acid ethyl ester with silica gel; and
   adding a non-iodinated unsaturated fatty acid ethyl ester and sulfur dioxide ($SO_2$) to the iodinated unsaturated fatty acid ethyl ester,
   wherein the vegetable oil is soybean oil,
   wherein the non-iodinated unsaturated fatty acid ethyl ester is comprised in an amount of 0.1 to 2 wt % based on a total weight of the contrast agent, and
   wherein the sulfur dioxide is comprised in an amount of 0.001 to 0.02 wt % based on the total weight of the contrast agent.

2. The method of claim 1, wherein the transesterification reaction is performed by adding ethanol and a strong base to the vegetable oil.

3. The method of claim 1, wherein glycerol and saturated fatty acid ethyl ester are removed after the transesterification reaction.

4. The method of claim 1, wherein the iodination reaction is performed by adding gaseous hydrogen iodide (HI) to the unsaturated fatty acid ethyl ester.

* * * * *